United States Patent [19]

Bigham

[11] 4,309,347
[45] Jan. 5, 1982

[54] PENICILLANOYLOXYMETHYL PENICILLANATE 1,1,1',1'-TETRAOXIDE

[75] Inventor: Eric C. Bigham, Chapel Hill, N.C.

[73] Assignee: Pfizer Inc., New York, N.Y.

[21] Appl. No.: 185,849

[22] Filed: Sep. 10, 1980

Related U.S. Application Data

[63] Continuation-in-part of Ser. No. 39,539, May 16, 1979, Pat. No. 4,244,951.

[51] Int. Cl.$^3$ ............................................ C07D 499/00
[52] U.S. Cl. ........................... 260/245.2 R; 260/239.1; 424/270; 424/271
[58] Field of Search ................... 260/245.2 R; 424/270

[56] References Cited

U.S. PATENT DOCUMENTS 3,850,908 11/1974 Von Daehne et al. .......... 260/239.1
3,869,449 5/1975 Godtfredsen .................... 260/239.1

FOREIGN PATENT DOCUMENTS 881675 8/1980 Belgium .
2713683 10/1977 Fed. Rep. of Germany .
2824535 12/1978 Fed. Rep. of Germany .
1303491 1/1973 United Kingdom .

Primary Examiner—Natalie Trousof
Assistant Examiner—Vera C. Clarke
Attorney, Agent, or Firm—Charles J. Knuth; Peter C. Richardson; J. Trevor Lumb

[57] ABSTRACT

Penicillanoyloxymethyl penicillanate 1,1,1',1'-tetraoxide; a method of treating a bacterial infection in a mammalian subject using penicillanoyloxymethyl penicillanate 1,1,1',1'-tetraoxide and a beta-lactam antibiotic; and pharmaceutical compositions comprising a suspension of penicillanoyloxymethyl penicillanate 1,1,1',1'-tetraoxide in water.

1 Claim, No Drawings

PENICILLANOYLOXYMETHYL PENICILLANATE 1,1,1',1'-TETRAOXIDE

CROSS-REFERENCE TO RELATED APPLICATIONS

This application is a continuation-in-part of co-pending application Ser. No. 39,539, filed May 16, 1979, now U.S. Pat. No. 4,244,951.

BACKGROUND OF THE INVENTION

This invention relates to the chemotherapy of bacterial infections in mammalian subjects. More particularly it relates to penicillanoyloxylmethyl penicillanate 1,1,1',1'-tetraoxide, a new chemical substance useful in the field of antibacterial chemotherapy.

One of the most well-known and widely used of the classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. One useful beta-lactamase inhibitor is penicillanic acid 1,1-dioxide, the compound of the formula I:

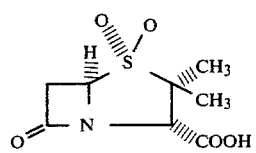
(I)

West German Offenlegungsschrift No. 2,824,535 describes the preparation of penicillanic acid 1,1-dioxide, and methods for its use as a beta-lactamase inhibitor in combination with beta-lactam antibiotics.

My co-pending application Ser. No. 39,539, filed May 16, 1979 now U.S. Pat. No. 4,244,951, discloses compounds of the formula

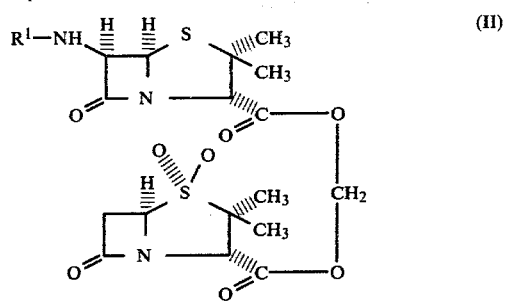
(II)

in which $R^1$ is an acyl group of an organic carboxylic acid, especially an acyl group from a natural, biosynthetic or semisynthetic penicillin compound. In one method of preparing the compounds of formula II, a carboxylate salt of a penicillin compound is reacted with a compound of the formula

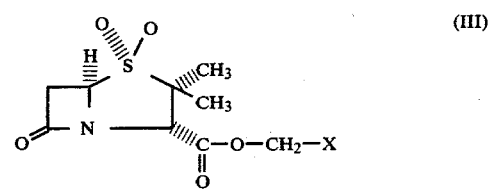
(III)

wherein X is a good leaving group. Examples of X are chloro, bromo, iodo, alkylsulfonyloxy, phenylsulfonyloxy and tolylsulfonyloxy. Example 25 of application Ser. No. 39,539 now U.S. Pat. No. 4,244,951 specifically describes the preparation of the compound of formula III, wherein X is chloro, by reaction of the diisopropylethylamine salt of penicillanic acid 1,1-dioxide with chloroiodomethane. However this reaction also produces the compound of the formula

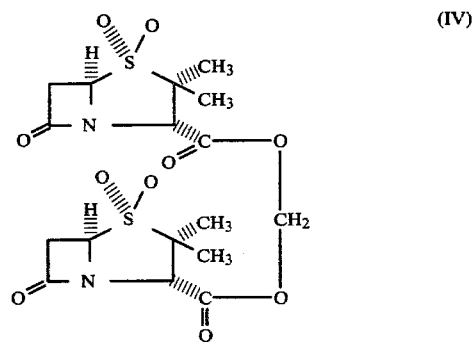
(IV)

and it has been found that the compound of formula IV acts as a bio-precursor of penicillanic acid 1,1-dioxide in mammalian, especially human, subjects.

Belgian Pat. No. 764,688, granted Mar. 23, 1971, and British Pat. No. 1,303,491, published Jan. 17, 1973, disclose: (a) certain 6'-acylaminopenicillanoyloxymethyl 6-acylaminopenicillanates; (b) certain 6'-acylaminopenicillanoyloxymethyl 6-aminopenicillanates; and (c) 6'-aminopenicillanoyloxymethyl 6-aminopenicillanate.

SUMMARY OF THE INVENTION

This invention provides penicillanoyloxymethyl penicillanate 1,1,1',1'-tetraoxide, the compound of the formula:

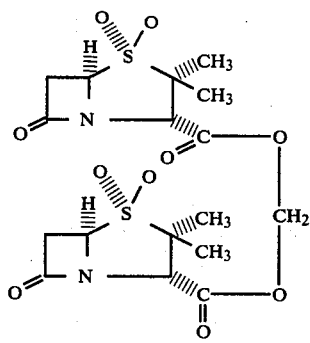
(IV)

The compound of the formula IV is converted into penicillanic acid 1,1-dioxide, a known beta-lactamase inhibitor, in vivo. Accordingly the compound of formula IV is useful for enhancing the activity of beta-lactam antibiotics in a mammalian subject, especially man. However, the compound of formula IV is sparingly soluble in water, and therefore it is particularly useful for the slow release of penicillanic acid 1,1-dioxide. Under these circumstances it is particularly valuable for use with slow release (depot) forms of beta-lactam antibiotics, especially the sparingly water soluble salts of penicillins.

Preferred sparingly water soluble penicillin antibiotic salts with which the compound of formula IV can be co-administered are procaine penicillin G, benzathine penicillin G, benethamine penicillin G, procaine penicillin V, benzathine penicillin V and benethamine penicillin V.

DETAILED DESCRIPTION OF THE INVENTION

This invention relates to derivatives of penicillanic acid, which is represented by the following structural formula

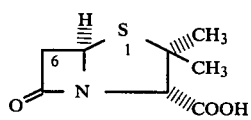
(V)

In formula V, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration.

Using this system, the compounds of formulae II and IV are named as derivatives of penicillanoyloxymethyl penicillanate (VI), in which primed and unprimed locants are used to distinguish between the two ring systems, viz.:

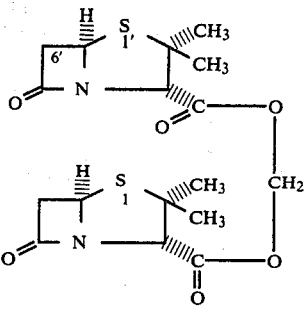
VI

Also, in this specification, reference is made to certain penicillin compounds, viz:

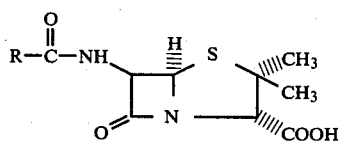

R is benzyl: penicillin G.
R is phenoxymethyl: penicillin V.

Procaine penicillin G is the 1:1 salt of penicillin G with 2-(N,N-diethylamino)ethyl 4-aminobenzoate, benzathine penicillin G is the 2:1 salt of penicillin G with N,N'-dibenzylethylenediamine and benethamine penicillin G is the 1:1 salt of penicillin G with N-benzyl-2-phenylethylamine. In like manner, procaine penicillin V is the 1:1 salt of penicillin V with 2-(N,N-diethylamino)ethyl 4-aminobenzoate, benzathine penicillin V is the 2:1 salt of penicillin V with N,N'-dibenzylethylenediamine and benethamine penicillin V is the 1:1 salt of penicillin V with N-benzyl-2-phenylethylamine.

In one method according to the invention, the compound of formula IV is prepared by reacting a carboxylate salt of the formula

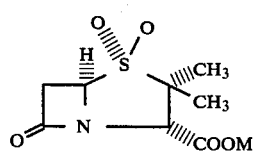
(VII)

with a compound of the formula III, wherein M is a carboxylate salt forming cation, and X is a good leaving group. A variety of cations can be used to form the carboxylate salt in the compound of formula VII, but salts which are commonly used include: alkali metal salts, such as sodium and potassium salts; alkaline earth metal salts, such as calcium and barium salts; and tertiary amine salts, such as trimethylamine, triethylamine, tributylamine, diisopropylethylamine, N-methylmorpholine, N-methylpiperidine, N-methylpyrrolidine, N,N'-dimethylpiperazine and N-methyl-1,2,3,4-tetrahydroquinoline salts. Typical examples of groups for X are chloro, bromo, iodo, alkylsulfonyloxy having one to four carbon atoms, phenylsulfonyloxy and tolylsulfonyloxy.

The reaction between a compound of formula VII and a compound of formula III is usually carried out by contacting the reagents in a solvent, at a temperature in the range from 0° to 80° C., and preferably from 25° to 50° C. The compounds of formula VII and III are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. Typical solvents which can be used include N,N-dimethylformamide, N,N-dimethylacetamide, N-methylpyrrolidone, dimethylsulfoxide and hexamethylphosphoramide. The reaction time varies according to a number of factors, but at about 40°–50° C. reaction times of several hours, e.g. 12 to 24 hours, are commonly used. When X is chloro or bromo, it is sometimes advantageous to add up to about one molar equivalent of an alkali metal iodide, which has the effect of speeding up the reaction.

The compound of formula IV is isolated in conventional fashion. When a water-miscible solvent is used, it is usually sufficient simply to dilute the reaction medium with an excess of water. The product is then extracted into a water immiscible solvent, such as ethyl acetate, and then the product is recovered by solvent evaporation. When a water immiscible solvent is used, it is usually sufficient to wash the solvent with water, and then recover the product by solvent evaporation. The compound of formula IV can be purified by well-known methods, such as recrystallization or chromatography, but due regard must be given to the lability of the beta-lactam ring system.

The compounds of formula III can be prepared from a compound of formula VII by reaction with a compound of the formula X—CH$_2$—Y, wherein M and X are as defined previously, and Y is a good leaving group. Y can be the same as or different than X, and typical groups for Y are chloro, bromo, iodo, alkylsulfonyloxy having one to four carbon atoms, phenylsulfonyloxy and tolylsulfonyloxy. This reaction is carried out in the same manner that was described for reaction of a compound of formula VII with a compound of formula III, except that it is preferable to use an excess of the compound of formula X—CH$_2$—Y (e.g. at least a fourfold excess).

Penicillanic acid, 1,1-dioxide and salts thereof (compounds of the formula VII) are prepared by published procedures (see West German Offenlegungsschrift No. 2,824,535).

Preparation of a compound of the formula IV has been described in terms of a two-step procedure which comprises reaction of a salt of penicillanic acid 1,1-dioxide with a compound of the formula X—CH$_2$—Y, to give a compound of formula III, followed by reaction of a compound of formula III with a further quantity of a salt of penicillanic acid 1,1-dioxide. As will be appreciated by one skilled in the art, it is possible effectively to combine these two steps into a single step simply by contacting a salt of penicillanic acid 1,1-dioxide with 0.5 molar equivalents of a compound of formula X—CH$_2$—Y, wherein X and Y are as defined previously. This reaction is carried out in the same manner as described previously for reaction of a compound of the formula VII with a compound of formula III.

As indicated hereinbefore the compound of formula IV acts as a bio-precursor to penicillanic acid 1,1-dioxide. In other words, when the compound of formula IV is exposed to mammalian blood or tissue, it is converted into penicillanic acid 1,1-dioxide. Under these circumstances, the compound of formula IV can be used to enhance the antibacterial effectiveness of beta-lactam antibiotics in mammals, particularly man. However, the compound of formula IV is sparingly soluble in water, and this makes it useful as a slow-release form of penicillanic acid 1,1-dioxide. Thus, administration of the compound of formula IV gives sustained blood levels of penicillanic acid 1,1-dioxide. Consequently, the compound of formula IV is especially useful for co-administration to a mammalian subject with slow-release forms of beta-lactam antibiotics, such as the salts of penicillins and cephalosporins which are sparingly soluble in water. Thus, the compound of formula IV can conveniently be administered to a mammalian subject as a single dose at approximately the same time as the subject first receives a dose of a sparingly water soluble penicillin antibiotic. Subsequent doses can be given as necessary to maintain the desired blood levels of penicillanic acid 1,1-dioxide. During treatment of a mammalian subject with the compound of formula IV and a sparingly water soluble penicillin antibiotic salt, the weight ratio of the compound of formula IV to the penicillin salt will be in the range from 6:1 to 1:6, and preferably 1:1 to 1:3.

In this context, a salt of a penicillin or cephalosporin is considered sparingly soluble in water if its solubility is in the range from 0.05 to 1.5 mg./ml. at about 25° C. Preferred sparingly-soluble beta-lactam antibiotic salts with which the compound of formula IV can be used are: procaine penicillin G, benzathine penicillin G, benethamine penicillin G, procaine penicillin V, benzathine penicillin V and benethamine penicillin V.

When considering use of the compound of formula IV as a slow-release form of penicillanic acid 1,1-dioxide, it is preferably administered subcutaneously. For this purpose, it is usual to prepare an aqueous suspension of the compound of the formula IV, in substantially the same manner as that currently used for formulation of a sparingly water-soluble salt of a beta-lactam antibiotic such as benzathine penicillin G. The proportional ratio of the compound of formula IV and the water can vary, depending on the dosage contemplated. However, aqueous suspensions of the compound of formula IV will usually contain from 50 to 200 milligrams of the compound of formula IV per milliliter of suspension. Small amounts of other ingredients conventionally used in preparing aqueous suspensions can also be added. For example, it is possible to add emulsifiers, such as lecithin, sorbitan mono-oleate, sorbitan monopalmitate and polyoxyethylene (20) sorbitan mono-oleate; hydrocolloids, such as carboxymethyl cellulose; dispersing agents, such as polyvinylpyrrolidone; and preservatives, such as sodium benzoate, methylparaben and propylparaben. Additionally it is preferable to buffer the suspension to a pH in the range from 6 to 7, and a sodium citrate/citric acid buffer is convenient for this purpose.

The prescribing physician will ultimately decide the appropriate dosage for a human subject when the compound of formula IV is being co-administered with a sparingly water-soluble salt of a beta-lactam antibiotic. This dosage will be expected to vary according to a variety of factors, such as the weight, age and response of the individual subject, as well as the nature and severity of the subject's symptoms and the particular sparingly water-soluble salt with which the compound of formula IV is being co-administered. However, single, subcutaneous doses of from about 4 to about 40 mg. per kilogram of body weight will normally be used. The dose will be repeated when the blood level of penicillanic acid 1,1-dioxide has fallen below the desired level.

EXAMPLE 1

Penicillanoyloxymethyl Penicillanate 1,1,1',1'-Tetraoxide

A mixture of 2.55 g of sodium penicillanate 1,1-dioxide, 3.3 ml. of bromochloromethane, a few milligrams of sodium iodide and 60 ml. of N,N-dimethylformamide was stirred at 40° to 50° C. overnight. The reaction mixture was cooled, and then it was poured into an excess of water. The resulting mixture was extracted with ethyl acetate, and the extracts were washed with water and dried ($Na_2SO_4$). Evaporation of the dried solution in vacuo afforded 0.44 g of penicillanoyloxymethyl penicillanate 1,1,1',1'-tetraoxide. The nuclear magnetic resonance spectrum of this product, in deuterochloroform, showed absorptions at 1.45 (singlet, 6H), 1.60 (singlet, 6H), 3.50 (multiplet, 4H), 4.50 (singlet, 2H), 4.80 (multiplet, 2H) and 6.00 (singlet, 2H) ppm downfield from internal tetramethylsilane.

The penicillanoyloxymethyl penicillanate 1,1,1',1'-tetraoxide was recrystallized from chloroform, giving 0.18 g. of material having a melting point of 185°–187° C. The infrared spectrum, as a potassium bromide disc, showed significant absorptions at 1800, 1325, 1212, 1143, 1117, 1005 and 948 $cm^{-1}$.

EXAMPLE 2

Penicillanoyloxymethyl Penicillanate 1,1,1',1'-Tetraoxide

A mixture of 2.55 g. of sodium penicillanate 1,1-dioxide, 0.41 ml. of diiodomethane and 30 ml. of N,N-dimethylformamide is stirred at 25° C. for 2 hours and then at 40° C. for an additional 4 hours. The reaction mixture is cooled and then it is poured into an excess of water. The resulting mixture is extracted with ethyl acetate, and the extracts are washed with water and dried ($Na_2SO_4$). Evaporation of the dried solution in vacuo affords penicillanoyloxymethyl penicillanate 1,1,1',1'-tetraoxide.

EXAMPLE 3

Formulation

A typical formulation contains the following ingredients:

| Ingredient | Weight (in grams) |
| --- | --- |
| Sodium benzoate | 0.3 |
| Sodium citrate | 0.45 |
| Citric acid | 0.05 |
| Lecithin | 0.3 |
| Sodium carboxymethyl cellulose | 0.5 |
| Polyoxyethylene (20) sorbitan mono-oleate | 0.07 |
| Penicillanoyloxymethyl penicillanate 1,1,1',1'-tetraoxide | 15.0 |

The above ingredients are combined and the volume is made up to 100 ml. with deionized water. An appropriate volume is used to provide the dosage required.

I claim:

1. Penicillanoyloxymethyl penicillanate 1,1,1',1'-tetraoxide.

* * * * *